(12) United States Patent
Hansen et al.

(10) Patent No.: US 10,369,034 B2
(45) Date of Patent: Aug. 6, 2019

(54) MEDICAL DEVICE INTRODUCER ASSEMBLY PARTICULARLY FOR BRANCHED MEDICAL DEVICES

(71) Applicant: COOK MEDICAL TECHNOLOGIES LLC, Bloomington, IN (US)

(72) Inventors: Palle M. Hansen, Bjaeverskov (DK); Per Hendriksen, Herlufmagle (DK); Erik E. Rasmussen, Slagelse (DK)

(73) Assignee: Cook Medical Technologies LLC, Bloomington, IN (US)

( * ) Notice: Subject to any disclaimer, the term of this patent is extended or adjusted under 35 U.S.C. 154(b) by 257 days.

(21) Appl. No.: 15/605,483

(22) Filed: May 25, 2017

(65) Prior Publication Data

US 2017/0348126 A1    Dec. 7, 2017

(30) Foreign Application Priority Data

Jun. 1, 2016  (GB) .................................. 1609585.3

(51) Int. Cl.
| | | |
|---|---|---|
| *A61F 2/97* | (2013.01) | |
| *A61F 2/966* | (2013.01) | |
| *A61F 2/954* | (2013.01) | |
| *A61F 2/07* | (2013.01) | |
| *A61F 2/06* | (2013.01) | |

(Continued)

(52) U.S. Cl.
CPC .................. *A61F 2/97* (2013.01); *A61F 2/07* (2013.01); *A61F 2/954* (2013.01); *A61F 2/966* (2013.01); *A61F 2002/065* (2013.01); *A61F 2002/9517* (2013.01); *A61M 25/0668* (2013.01); *A61M 2025/0675* (2013.01)

(58) Field of Classification Search
CPC .... A61F 2/97; A61F 2/07; A61F 2/966; A61F 2/954; A61F 2002/9517; A61F 2002/065; A61M 2025/0675; A61M 25/0668
USPC ................................................ 623/1.11, 1.12
See application file for complete search history.

(56) References Cited

U.S. PATENT DOCUMENTS 5,647,857 A    7/1997   Anderson et al.
5,693,083 A *  12/1997  Baker .................... A61B 17/11
                                                      606/195

(Continued)

FOREIGN PATENT DOCUMENTS

WO    WO2010/022516    3/2010
WO    2014/025853 A1   2/2014

OTHER PUBLICATIONS

Extended Search Report in corresponding European Application No. 17275038.2, dated Jul. 14, 2017, 8 pages.

(Continued)

*Primary Examiner* — Julian W Woo
(74) *Attorney, Agent, or Firm* — Brinks Gilson & Lione

(57) ABSTRACT

An introducer assembly includes a distal sheath and a proximal sheath. A splitting element is located at a proximal end of the distal sheath and is arranged to split the distal sheath in a distal direction, so as to deploy first a branch element of a medical device and thereafter the distal end of the medical device. The proximal sheath can then be retracted to release the proximal end of the medical device. Deployment of the medical device from the branch element first enables accurate positioning of the branch element prior to deployment of the main body portion of the medical device.

20 Claims, 5 Drawing Sheets

(51) Int. Cl.
*A61F 2/95* (2013.01)
*A61M 25/06* (2006.01)

(56) References Cited

U.S. PATENT DOCUMENTS

| | | | |
|---|---|---|---|
| 6,447,540 | B1 | 9/2002 | Fontaine et al. |
| 8,986,361 | B2 * | 3/2015 | Bortlein ............... A61F 2/2436 623/1.11 |
| 9,572,699 | B2 * | 2/2017 | Liu ......................... A61F 2/958 |
| 10,166,095 | B2 * | 1/2019 | Hartley .................... A61F 2/07 |
| 2002/0156518 | A1 | 10/2002 | Tehrani |
| 2008/0167705 | A1 | 7/2008 | Agnew |
| 2011/0301689 | A1 | 12/2011 | Dorn et al. |
| 2012/0010563 | A1 | 1/2012 | Ravikumar |
| 2012/0232637 | A1 | 9/2012 | Demetriades et al. |
| 2013/0041451 | A1 | 2/2013 | Patterson et al. |
| 2013/0226276 | A1 | 8/2013 | Newell et al. |
| 2015/0359651 | A1 | 12/2015 | Wubbeling |

OTHER PUBLICATIONS

Combined Search and Examination Report for GB1609585.3 dated Nov. 24, 2016, 7 pgs.
Response to Combined Search and Examination Report for GB1609585.3 filed Feb. 10, 2017, 22 pgs.
Examination Report for GB1609585.3 dated Feb. 24, 2017, 4 pgs.

* cited by examiner

MEDICAL DEVICE INTRODUCER ASSEMBLY PARTICULARLY FOR BRANCHED MEDICAL DEVICES

RELATED APPLICATION

This application claims the benefit of priority under 35 U.S.C. § 119(a) to Great Britain Patent Application No. GB 1609585.3, filed Jun. 1, 2016, which is hereby incorporated by reference in its entirety.

BACKGROUND

1. Technical Field

The present invention relates to an introducer assembly for deploying an implantable medical device in a vessel or other organ of a patient. The preferred embodiments are particularly suitable for deploying a branched, or bifurcated medical device such as a stent or stent graft.

2. Description of the Related Art

Implantable medical devices such as stents, stent grafts, vascular filters, plugs and so on are in common use. These devices are advantageously deployed endoluminally through the patient's vasculature from a remote percutaneous entry point such as the femoral artery or jugular vein. More recently, transapical access to the aorta has been used, and this technique is equally applicable to the teachings herein. The Seldinger technique is often used for such procedures. The devices are typically carried on an elongate introducer assembly which includes an elongate carrier element at the distal end of which the medical device is held during the deployment procedure. The introducer assembly typically also includes a protective sheath which covers the medical device until it has been positioned at the deployment site. Once so positioned, the sheath is removed by withdrawing it or splitting it away from the medical device. The medical device can then be released into the patient. The device is conventionally held in a radially compressed condition on the introducer assembly and expands when released.

Conventional introducer assemblies are suitable for deploying standard medical devices, that is intended to be deployed in a single vessel of a patient. Often it is advantageous for the medical device to be branched, so as to lie across both a main vessel and a side branch or bifurcation. The deployment of such medical devices is more complex given that at least a part of the medical device needs to be deployed into a different vessel or lumen from other parts of the device. For such devices it is known to use complex introducer assemblies having individual elements designed specifically to handle different parts of the medical device, such as the main portion of the medical device and the or each branch, or to design the medical device to have separate components which are coupled together during the device implantation process. These solutions are complex, often requiring deployment from a plurality of percutaneous entry points and/or a double deployment procedure.

Some examples of prior art branched medical devices and deployment assemblies are disclosed in US 2002/0156518, US 2012/010563, U.S. Pat. No. 6,447,540, US 2011/0301689, US 2012/0232637, and U.S. Pat. No. 5,647,857.

SUMMARY OF THE INVENTION

The present invention seeks to an improved introducer assembly and method for deploying a medical device.

According to an aspect of the present invention there is provided an introducer assembly for deploying a medical device including an elongate carrier member having a proximal portion and a distal portion, the distal portion having a distal end and a medical device support zone; a first proximal sheath disposed over the proximal portion of the carrier and a second distal sheath disposed over the distal portion and over at least a part of the medical device support zone, the second sheath including a second sheath distal end and a second sheath proximal end, and a splitting mechanism cooperatively coupled to the second sheath and arranged to split the second sheath from its second sheath proximal end to its second sheath distal end.

The assembly taught herein includes a double protective sheath, in which each sheath element overlies a part of the medical device. The distal portion of the sheath is able to be split, in the distal direction, in order to expose, in the preferred embodiments, a medial part of the medical device first and particularly a branch element, such as a side branch, bifurcation or a fenestration. The apparatus, though, can be used with medical devices which are not necessarily branched, for instance where it is advantageous or desired to deploy the intermediate portion and/or the part of the medical device closest to the proximal end of the introducer first, hereinafter referred to as the proximal end of the device. The assembly of the preferred embodiments is also able to maintain the main portion of the medical device in a contracted condition in a first part of the deployment process, which enables the branch element to be properly positioned before release of the remainder of the medical device, whereupon the device will expand to the walls of the vessel. This can be effected in a single and common procedure without the need for secondary introducer assemblies or the need to use multiple percutaneous access points.

Advantageously, the assembly includes an introducer tip coupled to the distal end of the elongate carrier, the splitting mechanism including a drive element for driving the splitting mechanism towards the introducer tip. The drive element may be a wire or string. The wire or string preferably includes a proximal end located at a proximal end of the introducer assembly.

This arrangement can provide a simple and reliable mechanism for splitting the distal sheath portion.

Preferably, the introducer tip includes a recess for receiving the splitting element. The recess conceals the splitting element once used, thereby to ensure that the splitting mechanism does not snag on any part of the medical device or patient, especially during the process of removing the introducer assembly from the patient.

In the preferred embodiment, the splitting mechanism includes a cutting element which engages with the second sheath from the second sheath proximal end. The cutting element may be in the form of a cutting hook.

Advantageously, a distal end of the first proximal sheath is disposed over a proximal end of the second distal sheath prior to deployment. More particularly, the distal end of the first proximal sheath is preferably disposed over the splitting mechanism prior to deployment. The proximal sheath portion can therefore protect the patient from the splitting mechanism until the distal end of the introducer assembly has been located at the deployment site.

The second distal sheath is preferably separable from the introducer assembly. For this and other purposes, the second distal sheath may be made of biodegradable material.

In practice, the introducer assembly is preferably supplied with a medical device carried on the carrier, wherein a distal end of the medical device is deployable by splitting of the second distal sheath. In some embodiments, the medical device includes a branch section, the branch section being held by the second distal sheath prior to deployment. The medical device may be a branched stent graft.

Preferably, the first proximal sheath is slidable in a proximal direction relative to the carrier member for deploying a medical device carried in the introducer assembly.

According to another aspect of the present invention, there is provided apparatus including:

an introducer assembly for deploying a medical device including an elongate carrier member having a proximal portion and a distal portion, the distal portion having a distal end and a medical device support zone; a first proximal sheath disposed over the proximal portion of the carrier and a second distal sheath disposed over the distal portion and over at least a part of the medical device support zone, the second sheath including a second sheath distal end and a second sheath proximal end, and a splitting mechanism cooperatively coupled to the second sheath and arranged to split the second sheath from its second sheath proximal end to its second sheath distal end;

a medical device carried on the elongate carrier, the medical device including a proximal portion, a distal portion and an intermediate portion therebetween, wherein the medical device proximal portion is covered by the first proximal sheath and the distal portion is covered by the second distal sheath;

wherein the medical device is releasable from the introducer assembly by exposure first of the intermediate portion while at least the medical device proximal portion is held in the first proximal sheath.

The intermediate portion of the medical device may include a branch member, wherein the branch member is exposed while at least the medical device proximal portion is held in the first proximal sheath.

Preferably, the intermediate portion, or branch member, is at least partially covered by the second sheath.

The branch member may be a side branch, bifurcation or a fenestration. A side branch or bifurcation is typically a second stent or stent graft extending from a body portion of the medical device and provides a second lumen for passage of body fluids, particularly blood.

The medical device may include a body portion having an intermediate location at which the branch member is located, wherein the second distal sheath is splittable to release the branch member prior to release of a distal end of the body portion of the medical device. In the case that the branch member is a side branch, integral with the body portion, the side branch can be deployed which the main part of the medical device remains radially compressed on the introducer assembly, allowing for correct and unobstructed positioning of the side branch.

According to another aspect of the present invention, there is provided a method of deploying a medical device in a patient by means of an introducer assembly including an elongate carrier member having a proximal portion and a distal portion, the distal portion having a distal end and a medical device support zone; a first proximal sheath disposed over the proximal portion of the carrier and a second distal sheath disposed over the distal portion and over at least a part of the medical device support zone, the second sheath including a second sheath distal end and a second sheath proximal end, and a splitting mechanism cooperatively coupled to the second sheath and arranged to split the second sheath from its second sheath proximal end to its second sheath distal end; a medical device being carried on the elongate carrier, the medical device including a proximal portion, a distal portion and an intermediate portion, wherein the medical device proximal portion is covered by the first proximal sheath and at least the distal portion is covered by the second distal sheath;

wherein the method includes the steps of:

releasing the intermediate portion;

splitting the second distal sheath from the proximal end thereof to expose at least the distal portion of the medical device while at least the proximal portion of the medical device is held by the first proximal sheath, releasing the distal end of the medical device, and releasing the proximal end of the medical device.

Preferably, the medical device proximal portion is covered by the first proximal sheath and the distal portion and intermediate portion are covered by the second distal sheath; the method including the step of splitting the second distal sheath from the proximal end thereof to expose the intermediate portion while the proximal portion of the medical device is held by the first proximal sheath and the distal portion of the medical device is held by the second distal sheath.

Advantageously, the method includes the step of partially retracting the first proximal sheath prior to splitting of the second distal sheath in order to expose the splitting mechanism.

Preferably, the method includes the step of separating the second distal sheath from the introducer assembly.

In the preferred embodiment, the method includes the step of concealing the splitting mechanism into a recess of an element of the introducer assembly after splitting of the second distal sheath.

Other features and advantages of the teachings herein will become apparent from the description of the preferred embodiments which follows.

BRIEF DESCRIPTION OF THE DRAWINGS

Embodiments of the present invention are described below, by way of example only, with reference to the accompanying drawings, in which.

DETAILED DESCRIPTION OF THE PREFERRED EMBODIMENTS

Figure 1:
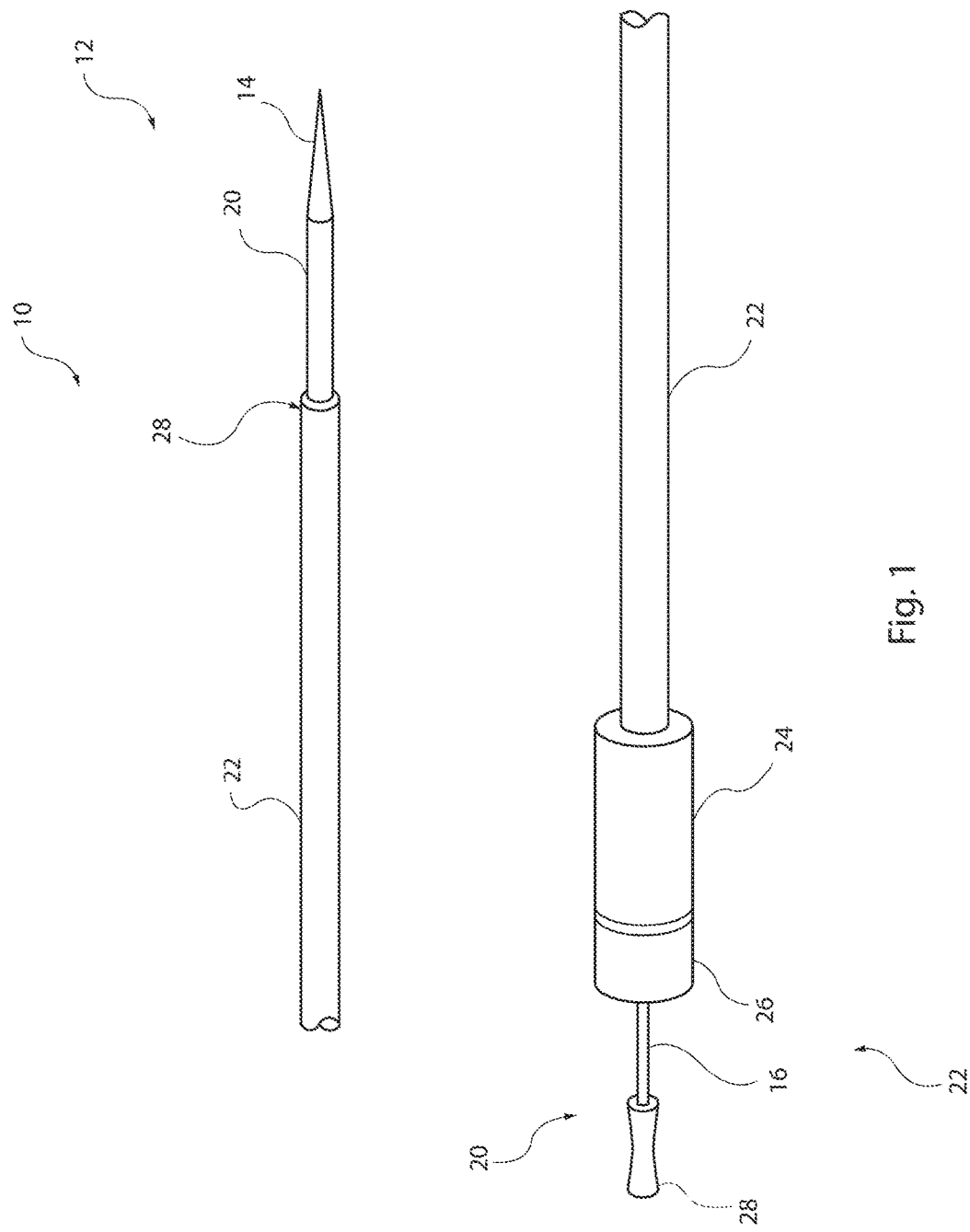
FIG. 1 is a schematic diagram of an embodiment of introducer assembly according to the teachings herein.

The accompanying drawings show in schematic form a preferred embodiment of introducer assembly and device according to the teachings herein. The skilled person will appreciate that the drawings do not depict all of the components of the introducer assembly, for the sake of clarity, with minor components or otherwise components not relevant to the teachings herein not being shown or described. Such components are well known in the art or otherwise will be readily appreciated by the skilled person and therefore no explicit or detailed discussion thereof is necessary.

It is also to be understood that the drawings are not to scale and often elements are shown enlarged in order to show certain elements clearly. The skilled person will be fully aware of the suitable scale, proportion and size of the elements of the assembly, and also that these will differ from one medical application to another.

The term "distal" as used herein is to be understood with regard to the introducer assembly and components thereof as being furthest from the physician during the medical procedure. For the sake of clarity of description the term is use in the same manner for a medical device carried on the introducer assembly.

Similarly, the term "proximal" as used herein is to be understood with regard to the introducer assembly and components thereof as being closest to the physician during the medical procedure and for the sake of clarity the term is used in the same manner in relation to a medical device carried on the introducer assembly.

The term "branch element" as used herein includes a side branch, for instance as shown in the examples of medical device shown in the drawings and described below, a bifurcation or a fenestration.

Referring first to FIG. 1, this shows in schematic form an embodiment of introducer assembly 10 according to the teachings herein. The skilled person will appreciate that what is shown in the drawings is in schematic form only and the drawing is not intended to depict portions or sizes of the various components. At the distal end 12 of the introducer assembly 10 there is provided a flexible tip 14, which is in this embodiment attached to an elongate carrier element 16, which extends from the proximal end 18 of the introducer assembly 10 to the distal end 12. Disposed at the distal end 12 of the assembly 10 there is also provided a distal sheath 20, as described in further detail below. A proximal sheath 22 extends from a proximal end of the distal sheath 20 to the proximal end 18 of the assembly 10 and in practice is fixed to a handle assembly 22, which may have characteristics conventional in the art. In this schematic depiction, the handle assembly 22 includes a distal handle portion 24 and a proximal handle portion 26. The proximal handle portion 26 is coupled to a splitting mechanism (not shown in FIG. 1 but shown in later Figures and described in further detail below) for splitting the distal sheath 20 in accordance with the teachings herein.

The handle assembly 22 also includes a carrier handle 28 for manipulating the position of a medical device carried at the distal end 12 of the introducer assembly 10 relative to the proximal sheath 22 in particular, in order to complete release of the medical device from the introducer assembly. The introducer assembly 10 will typically have a length from around a few tens of centimetres to a metre or more, dependent upon the medical device carried by the introducer assembly, the location in which it is to be deployed within a patient and the position of the percutaneous access point into the patient. For example only, where access is through the femoral artery, the introducer assembly will be relatively long, whereas for access through the jugular vein, for example, the assembly may be significantly shorter. These parameters are well within the common general knowledge of the skilled person.

As will become apparent in further detail below, the distal sheath 20 has an outer diameter which is sufficiently small so as to fit within a distal end 28 of the proximal sheath 22. In some embodiments, this relationship of diameters of the distal and proximal sheaths 20, 22 may differ and in particular such that the distal sheath 20 does not reside partially within the proximal sheath 22, although the latter is not preferred.

Figure 2:
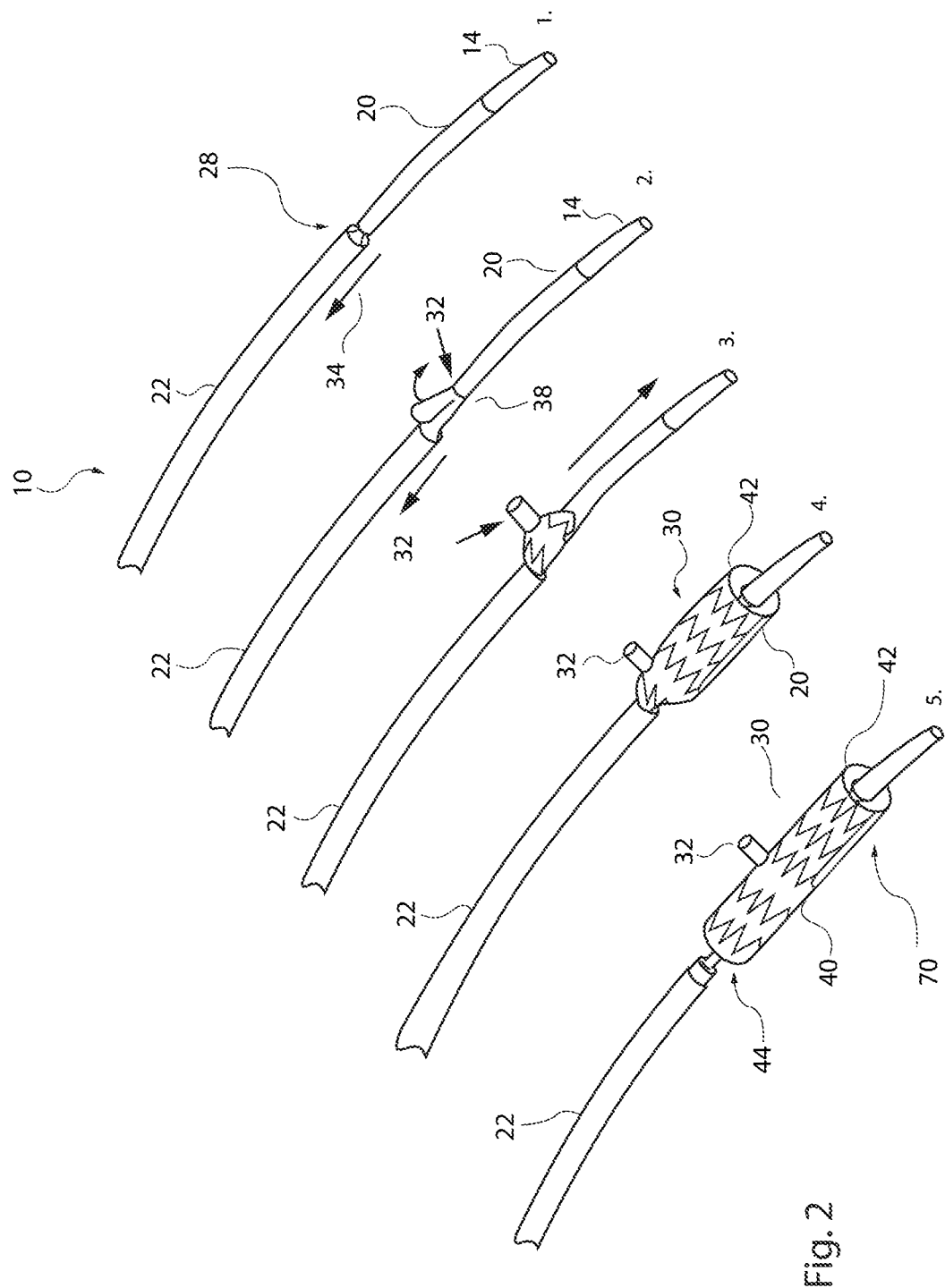
FIG. 2 shows various views of the assembly of FIG. 1 during the process of deploying a branched stent graft carried in the introducer assembly.

Referring now to FIG. 2, this shows in schematic form the steps of deploying a branched stent graft 30, having a in an intermediate portion thereof a side branch 32, from the introducer assembly 10. Referring to FIG. 2.1, in a first stage, the proximal sheath 22 is retracted in a proximal direction (by manipulation of the handle portions 24 and 28) so as to separate the distal and proximal sheaths 20, 22, potentially forming a gap between them. The direction of movement can be seen at arrow 34 in FIG. 2.1.

Referring now to FIG. 2.2, once the proximal sheath 22 has been retracted relative to the distal sheath 20 by a sufficient amount, the intermediate portion, in this example the side branch 32, of the medical device 30 is able to deploy radially outwardly. In some embodiments this may be because the side branch 32 is located proximal of the proximal end 38, whereas the other embodiments the side branch 32 may be disposed within the distal sheath 20 and released only as the distal sheath 20 is split open, as described in further detail below.

Referring to FIG. 2.3, as can be seen, the side branch 32 is fully deployed and the process can move to deploying the main body portion 40 of the stent graft, by further splitting of the distal sheath 20. As will be apparent in particular in FIG. 2.3, as the side branch 32 is deployed first and before the body portion 40 of the stent graft 30 is radially expanded, it is possible to adjust the positioning and orientation of the side branch 32 within the vessel of a patient. More specifically, the medical device 30 can be moved while still held contracted on the introducer assembly 20 until the side branch is aligned both longitudinally and radially relative to a branch vessel into which the side branch 32 is intended to be positioned.

With reference now to FIG. 2.4, the distal part 32 of the stent graft 30 can be seen in its radially expanded condition, that is released from the carrier of the introducer assembly, whereas the proximal end of the stent graft 30 remains constrained within the proximal sheath 22. With reference to FIG. 2.5, the proximal sheath 22 has been retracted further in order to release the proximal portion 44 and thus to release the medical device 30 from the introducer assembly 10. FIGS. 2.4 and 2.5 show the distal sheath 20 having been split longitudinally, with the sheath 20 separating from the introducer assembly to be carried with the expanding medical device 30 to be held against the vessel wall once the medical device has been deployed. The sheath 20 is preferably, though not necessarily, made of a biodegradable or bioresorbable material.

As will be apparent from the sequence of steps shown in FIGS. 2.1 to 2.5, the assembly 10 provides for the deployment of a medical device from its branch element first and then the distal end of the medical device prior to release of the proximal end. The medical device 30 can be deployed much more smoothly while retaining the ability to position accurately the side branch into or with respect to a branch vessel, without requiring a secondary medical procedure or second introducer assembly to locate the side branch 32 (or aligning any other branch element) into a branch vessel.

While FIG. 2 and the remaining Figures and accompanying description are directed to a branched stent graft, the teachings herein are equally applicable to bifurcated stent grafts and stent grafts having side fenestrations.

Figure 3:
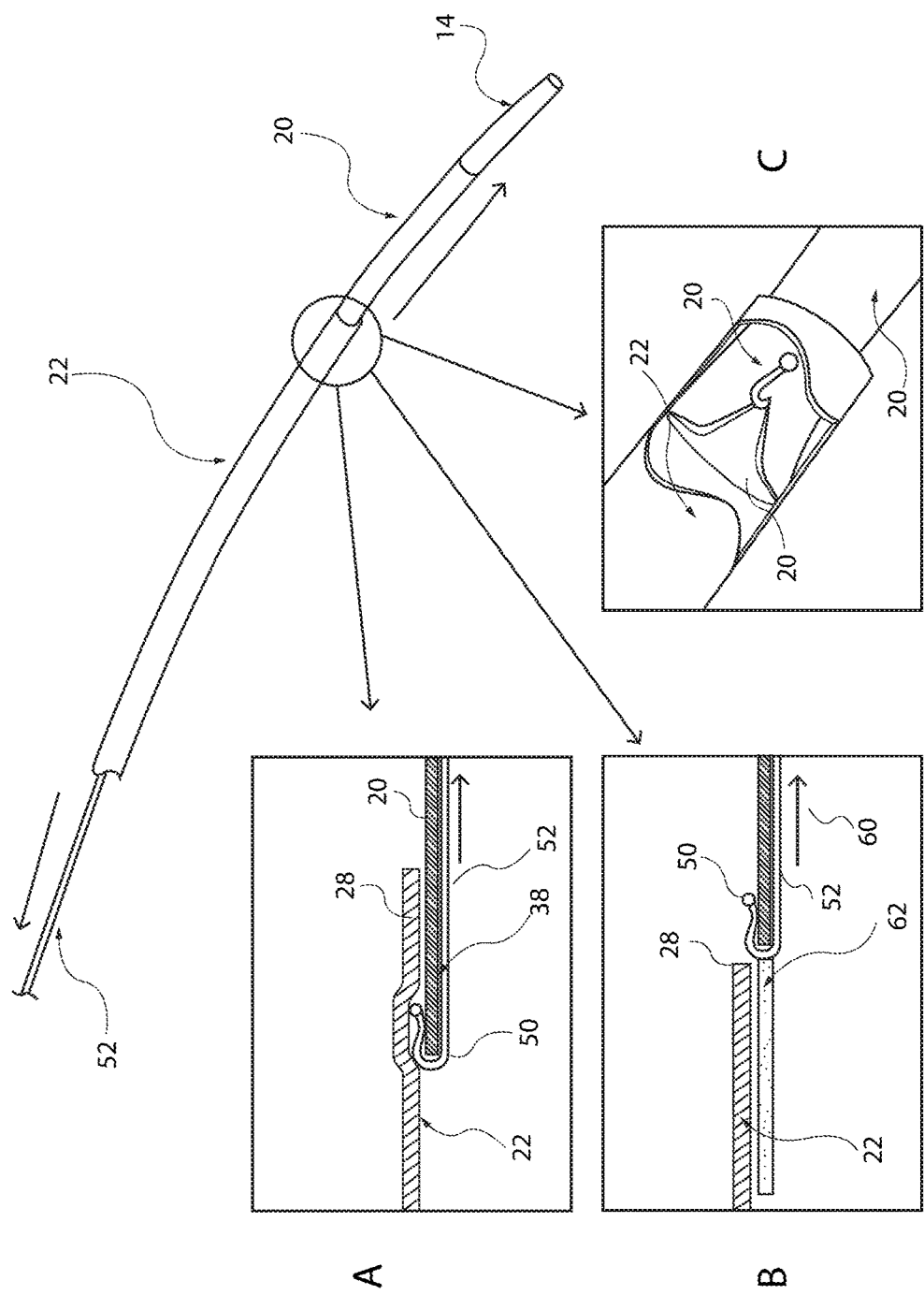
FIG. 3 shows various views of the preferred splitting mechanism of the assembly of FIGS. 1 and 2.

Referring now to FIG. 3, this shows in better detail the construction of the distal end 12 of the introducer assembly 10. FIGS. 3A-3C show different views of the encircled portion of the assembly 10 of FIG. 3 and in particular of the proximal end 38 of the distal sheath 20 and the distal end 28 of the proximal sheath 22. With reference first to FIG. 3A, the assembly 10 is provided with a splitting mechanism 50 which in this example is in the form of a hook having a rounded hook end which is located over the proximal end 38 of the distal sheath 20. The hook 50 is attached to a wire 52 which, as explained in further detail below, extends to the tip 14 of the assembly 10 and back through the assembly 10 to a proximal position and in particular to the handle portion 26 of the handle assembly 22 (seen in FIG. 1). The hook 50 is sufficiently strong to be able to tear through the wall of the distal sheath 20, in the manner depicted in FIGS. 3B and 3C. For this purpose, the distal sheath 20 may be weakened for instance by a weakening line, by having a preliminary slit cut therewithin, by a preferential tearing characteristic to the material forming the distal sheath, and so on. In many embodiments no specific weakening provision is required, particularly when the sheath 20 is made of a thin wall, which can be expected to be readily splittable by the splitting element 50.

As will be apparent from FIG. 3A, the distal end 28 of the proximal sheath 22 preferably overlies the hook 50 as well as the proximal end 38 of the distal sheath 20, so as to safeguard the cutting element 50 and also the patient's vessels during introduction of the distal end of the introducer assembly into the patient's vasculature.

Retraction of the handle element 26 relative to the proximal sheath handle 24 causes the wire 52 to be pulled back, thereby pulling the cutting hook 50 towards the dilator tip 14, splitting the distal sheath 20 from its proximal end 38 first, as can be seen schematically in Figure C. The outer sheath 22 is shown partially cut away in FIG. 3C in order to show the hook 50 splitting the distal sheath 20.

With reference to FIG. 3B, the hook 50 can be pulled further, in the direction of arrow 60, that is in a direction towards the distal tip 14. Once the split 62 in the distal sheath 20 is sufficiently long to extend beyond the distal end 28 of the proximal sheath 22, the side arm 32 of the medical device held in the introducer assembly (see FIG. 2) is able to expand radially outwardly, as shown in FIG. 2.2.

As described above, in the alternative or additionally, the proximal sheath 22 can be retracted at this stage so as to expose most of or all of the proximal end 38 of the distal sheath 20, in order to assist in the deployment of the side branch 32 of the medical device 30 or of any other branch element.

Figure 4:
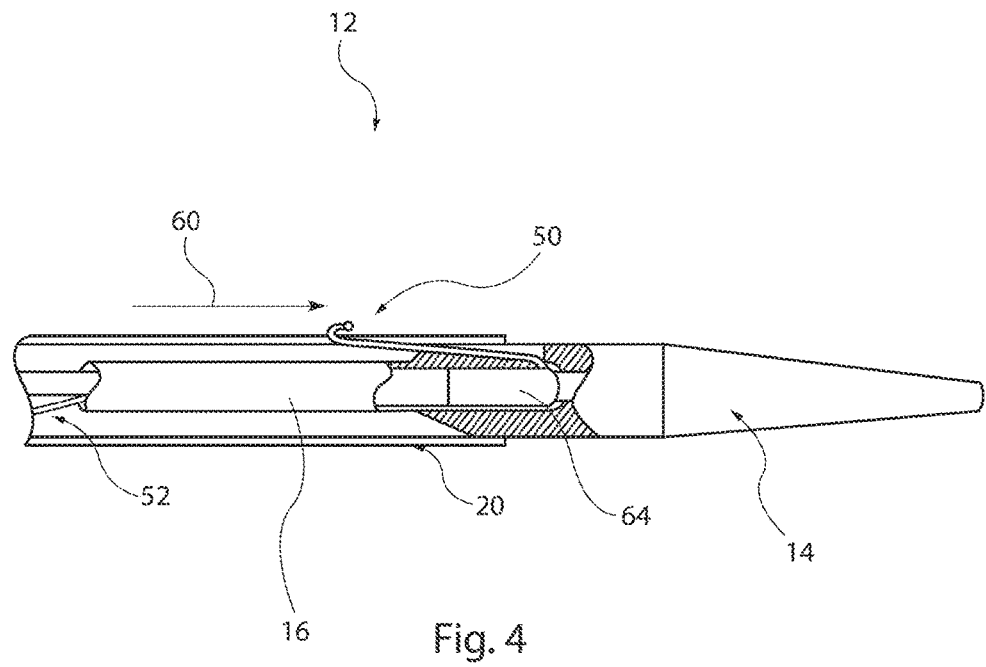
FIGS. 4 to 6 show further views of the splitting mechanism and of the distal end of the assembly of FIGS. 1 to 3.

Referring now to FIG. 4, this is a part cross-sectional view of the distal end 12 of the introducer assembly similar to the views of FIG. 3. The splitting hook 50 can be seen having formed a split through the majority of the length of the distal sheath 20. The wire 52 extends over and around a rounded guide element 64 which may form part of the elongate device carrier 16, of the distal tip 14 or any other suitable component of the introducer assembly 10. The guide element 64 enables the wire 52 to curve in a U, back to the proximal end 20 of the introducer assembly 10.

Figure 5:
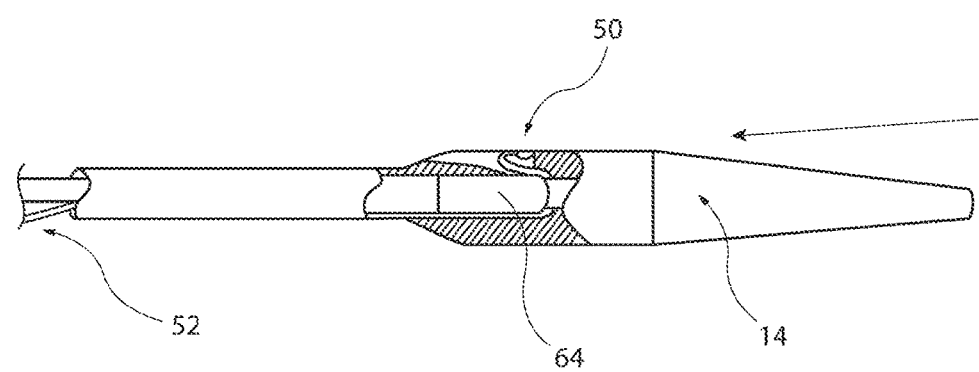
Figure 6:
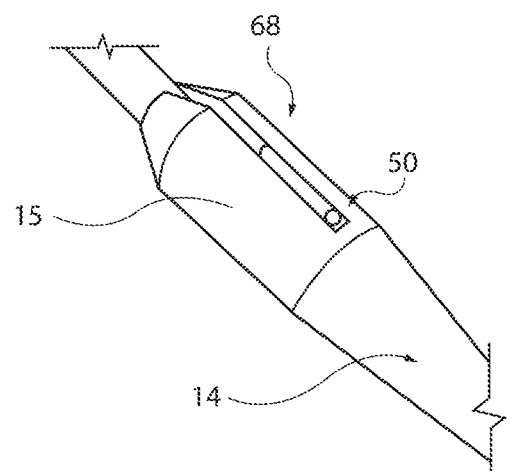

Referring now to FIGS. 5 and 6, in the preferred embodiment the dilator tip 14 includes an elongate slot 68 in a portion 15 of the dilator tip having a greater radial thickness. The portion 15 is at the proximal end of the dilator tip 14. The slot 68 is preferably deep enough so as to accommodate the entirety of the hook 50, such that the hook 50 sits within the periphery of the distal tip 14 when held in the slot 68. In FIG. 6 it can be seen that the slot 68 has a depth which is greater than the width of the hook 50 and significantly longer than the length of the hook 50. As will be apparent from the cross-sectional view of FIG. 5, the rounded guide member 64 is, in the preferred embodiment, located within the distal tip 14, thereby ensuring proper location of the hook 50 into the slot 68 as the wire 52 is pulled back.

Figure 7:
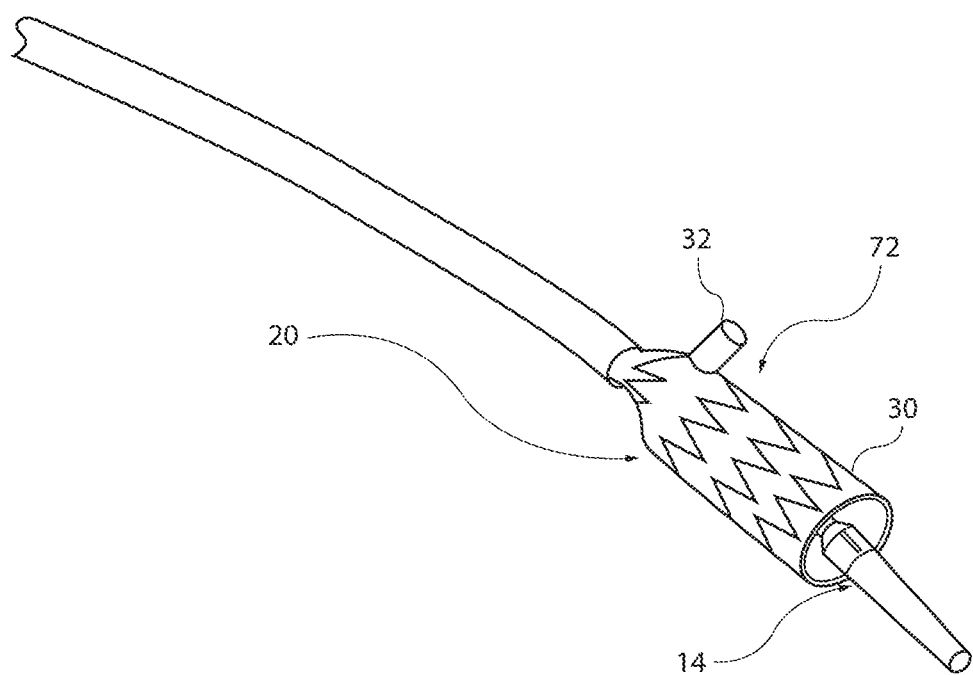
FIG. 7 shows the distal end of the assembly with the medical device in the process of being completely released form the assembly.

With reference now to FIG. 7, securing the hook 50 into the distal tip 14 after the distal sheath 20 has been split and the medical device 30 deployed within the lumen enables the distal tip, with the hook 50, to be withdrawn through the length of the medical device 30 without risk of snagging the hook 50 into the medical device.

In the arrangement disclosed above the branch element 32 of the medical device 30 is held within the distal sheath 20 and deployable when the distal sheath is split by the splitting device 50. In other embodiments the branch element 30 may be held within the proximal sheath 22 and released on retraction of the proximal sheath. In this event, the proximal and distal sections of the medical device 30 will be held radially constrained, until splitting of the distal sheath 20 and further retraction of the proximal sheath.

It will be apparent that although in the embodiments shown the distal end of the medical device 30 is deployed first, in other embodiments this may be the other way around, that is by retracting the proximal sheath 22 first to release the proximal end of the medical device and subsequently splitting of the distal sheath 20 to release the distal end of the medical device 30. this latter alternative is, however, not preferred.

In summary, therefore, the introducer assembly 10 includes a distal sheath 20 and a proximal sheath 22. A splitting element 50 is located at a proximal end 38 of the distal sheath 20 and is arranged to split the distal sheath 20 in a distal direction, so as to deploy first the branch element 32 of the medical device 30 and thereafter the distal end of the medical device 30. The proximal sheath 22 can then be retracted to release the proximal end of the medical device 30. Deployment of the medical device from the branch element 32 first enables accurate positioning of the branch element 32 prior to deployment of the main body portion 40 of the medical device.

The deployment procedure and associated apparatus also have the additional advantage of requiring fewer barbs 72 on the medical device 30 compared to prior art devices, which are deployed from one end of the device rather than from a branch element first. In this embodiment, deploying the branch element 32 initially and providing for its proper alignment, with then gradual release of the medical device 30 from an intermediate position thereof, will often require no anchoring barbs to be used. Where these are advantageous or desired they can be positioned as shown in FIG. 7 (barbs 72) only around the middle of the body portion of the medical device 30. A reduction in the number of barbs used reduces trauma and damage to the vessel wall and reduces the risk of consequential medical complications.

As described above, the apparatus taught herein can be used with medical devices which are not necessarily branched, for instance where it is advantageous or desired to deploy the part of the medical device closest to the proximal end of the introducer first, referred herein to as the proximal end of the device. Examples include medical devices having a different structure or different characteristics at its proximal end relative to it distal end, and/or where it is most important to position accurately the proximal end of the device first (i.e. the end closest to the proximal end of the introducer assembly).

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

What is claimed is:

1. An introducer assembly for deploying a medical device, the assembly including an elongate carrier member having a proximal portion and a distal portion, the distal portion having a distal end and a medical device support zone; a first proximal sheath disposed over the proximal portion of the carrier member and a second distal sheath disposed over the distal portion and over at least a part of the medical device support zone, the second sheath including a second sheath distal end and a second sheath proximal end, and a splitting mechanism cooperatively coupled to the second sheath and arranged to split the second sheath from its second sheath proximal end to its second sheath distal end.

2. The introducer assembly according to claim 1, including an introducer tip coupled to the distal end of the elongate carrier member, the splitting mechanism including a drive element connected at the introducer tip for pulling the splitting mechanism towards the introducer tip.

3. The introducer assembly according to claim 2, wherein the drive element is a wire or string.

4. The introducer assembly according to claim 2, wherein the introducer tip includes a recess for receiving the splitting element.

5. The introducer assembly according to claim 1, wherein the splitting mechanism includes a cutting element which engages with the second sheath from the second sheath proximal end.

6. The introducer assembly according to claim 5, wherein the cutting element is in the form of a cutting hook.

7. The introducer assembly according to claim 1, wherein a distal end of the first proximal sheath is disposed over a proximal end of the second distal sheath prior to deployment.

8. The introducer assembly according to claim 1, wherein the second distal sheath is separable from the introducer assembly.

9. The introducer assembly according to claim 1, including a medical device carried on the carrier member, wherein a distal end of the medical device is deployable by splitting the second distal sheath.

10. The introducer assembly according to claim 9, wherein the medical device includes a branch section, the branch section being held by the first or the second distal sheath prior to deployment.

11. The introducer assembly according to claim 9, wherein the medical device is a branched stent graft.

12. The introducer assembly according to claim 1, wherein the first proximal sheath is slidable in a proximal direction relative to the carrier member for deploying a medical device carried in the introducer assembly.

13. A medical apparatus including:
an introducer assembly for deploying a medical device, the assembly including an elongate carrier member having a proximal portion and a distal portion, the distal portion having a distal end and a medical device support zone; a first proximal sheath disposed over the proximal portion of the carrier member and a second distal sheath disposed over the distal portion and over at least a part of the medical device support zone, the second sheath including a second sheath distal end and a second sheath proximal end, and a splitting mechanism cooperatively coupled to the second sheath and arranged to split the second sheath from its second sheath proximal end to its second sheath distal end;
a medical device carried on the elongate carrier member, the medical device including a proximal portion, a distal portion and an intermediate portion therebetween, wherein the medical device proximal portion is covered by the first proximal sheath and the distal portion is covered by the second distal sheath;
wherein the medical device is releasable from the introducer assembly by exposure first of the intermediate portion while at least the medical device proximal portion is held in the first proximal sheath.

14. The apparatus according to claim 13, wherein the intermediate portion includes a branch member, wherein the branch member is exposed while at least the medical device proximal portion is held in the first proximal sheath.

15. The apparatus according to claim 14, wherein the branch member is at least partially covered by the second sheath.

16. A method of deploying a medical device in a patient by means of an introducer assembly including an elongate carrier member having a proximal portion and a distal portion, the distal portion having a distal end and a medical device support zone; a first proximal sheath disposed over the proximal portion of the carrier member and a second distal sheath disposed over the distal portion and over at least a part of the medical device support zone, the second sheath including a second sheath distal end and a second sheath proximal end, and a splitting mechanism cooperatively coupled to the second sheath and arranged to split the second sheath from its second sheath proximal end to its second sheath distal end; a medical device being carried on the elongate carrier member, the medical device including a proximal portion, a distal portion and an intermediate portion, wherein the medical device proximal portion is covered by the first proximal sheath and at least the distal portion is covered by the second distal sheath;
wherein the method includes the steps of:
releasing the intermediate portion;
splitting the second distal sheath from the proximal end thereof to expose at least the distal portion of the medical device while at least the proximal portion of the medical device is held by the first proximal sheath, releasing the distal end of the medical device, and releasing the proximal end of the medical device.

17. The method according to claim 16, wherein the intermediate portion includes a branch member, wherein the branch member is exposed while at least the medical device proximal portion is held in the first proximal sheath.

18. The method according to claim 17, wherein the medical device proximal portion is covered by the first proximal sheath and the distal portion and branch member are covered by the second distal sheath; the method including the steps of:
splitting the second distal sheath from the proximal end thereof to expose the branch member while the proximal portion of the medical device is held by the first proximal sheath and the distal portion of the medical device is held by the second distal sheath.

19. The method according to claim 16, including the step of partially retracting the first proximal sheath prior to splitting of the second distal sheath in order to expose the splitting mechanism.

20. The method according to claim 16, including the step of separating the second distal sheath from the introducer assembly.

\* \* \* \* \*